US010105455B2

(12) United States Patent
Duvall et al.

(10) Patent No.: US 10,105,455 B2
(45) Date of Patent: Oct. 23, 2018

(54) FLUOROCOXIB A LOADING INTO ROS-RESPONSIVE NANOPARTICLES

(71) Applicant: Vanderbilt University, Nashville, TN (US)

(72) Inventors: Craig L. Duvall, Nashville, TN (US); Lawrence J. Marnett, Nashville, TN (US); Jashim Uddin, Nashville, TN (US); Thomas A. Werfel, Nashville, TN (US); Mukesh Gupta, Nashville, TN (US); Brenda C. Crews, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/206,798

(22) Filed: Jul. 11, 2016

(65) Prior Publication Data

US 2017/0007723 A1   Jan. 12, 2017

Related U.S. Application Data

(60) Provisional application No. 62/191,367, filed on Jul. 11, 2015.

(51) Int. Cl.
| | | |
|---|---|---|
| *A61K 49/00* | (2006.01) | |
| *A61K 9/00* | (2006.01) | |
| *A61K 47/34* | (2017.01) | |
| *A61K 9/51* | (2006.01) | |

(52) U.S. Cl.
CPC ........ *A61K 49/0052* (2013.01); *A61K 9/0019* (2013.01); *A61K 9/5146* (2013.01); *A61K 47/34* (2013.01); *A61K 49/0041* (2013.01); *A61K 49/0082* (2013.01)

(58) Field of Classification Search
None
See application file for complete search history.

(56) References Cited

U.S. PATENT DOCUMENTS

| | | | |
|---|---|---|---|
| 7,736,624 B2 | 6/2010 | Uddin et al. | |
| 8,143,302 B2 | 3/2012 | Uddin et al. | |
| 8,865,130 B2 | 10/2014 | Uddin et al. | |
| 2014/0004050 A1* | 1/2014 | Rajadas | A61K 49/006 424/9.6 |

OTHER PUBLICATIONS

Alakhov, et al., "Block copolymer-based formulation of doxorubicin. From cell screen to clinical trials", Colloids and Surfaces B: Biointerfaces 16, 1999, 113-134.
Bertrand, et al., "Cancer Nanotechnology: The impact of passive and active targeting in the era of modern cancer biology", Adv. Drug Del. Rev. 66, 2014, 2-25.
Cabral, et al., "Accumulation of sub-100 nm polymeric micelles in poorly permeable tumors depends on size", Nature Nanotechnology 6, 2011, 815-823.
Convertine, et al., "Development of a novel endosomolytic diblock copolymer for siRNA delivery", J. Controlled Rel. 133(3), 2009, 221-229.
Coutinho et al., "Nile Red and DCM fluorescence anisotropy studies in C12E7/DPPC mixed systems", J. Phys. Chem. B 106, 2002, 12841-12846.
Crofford, et al., "Progress toward a new class of therapeutics: Selective COX-2 Inhibition", J. Rheumatology 49, 1997, 15-19.
Danhier, et al., To exploit the tumor microenvironment: Passive and active tumor targeting of nanocarriers for anti-cancer drug delivery, J. Controlled Rel. 148(2), 2010, 135-146.
Dubois, et al., "Cyclooxygenase-2 and epidermal growth factor receptor: Pharmacologic targets for chemoprevention", J Clin Oncology 23, 2005, 254-266.
Gao, et al., "In situ growth of a stoichiometric PEG-like conjugate at a protein's N-terminus with significantly improved pharmacokinetics", Proc. Natl. Acad. Sci. USA 106, 2009, 15231-15236.
Gao, et al., "In situ growth of a PEG-like polymer from the C terminus of an intein fusion protein improves pharmacokinetics and tumor accumulation", Proc. Natl. Acad. Sci. USA 107, 2010, 16432-16437.
Gao, et al., "pH-Responsive nanoparticles for drug delivery", Mol. Pharmaceutics 7(6), 2010, 1913-1920.
Gupta, et al., "Cell Protective, ABC triblock polymer-based thermoresponsive hydrogels with ROS-triggered degradation and drug release", J. Am. Chem. Soc. 136(42), 2014, 14896-14902.
Gupta, et al., "Cyclooxygenase-2 inhibitor therapy for the prevention of esophageal adenocarcinoma in Barrett's Esophagus", Natl. Cancer Inst. 94, 2002, 406-407.
Gupta, et al., "Poly(PS-b-DMA) micelles for reactive oxygen species triggered drug release", J. Controlled Rel. 162(3), 2012, 591-598.
Hu, et al., "Scavenging ROS: superoxide dismutase/catalase mimetics by the use of an oxidation-sensitive nanocarrier/enzyme conjugate", Bioconjugate Chem. 23(3), 2012, 438-439.
Hubbel, et al., "Nanomaterials for drug delivery", Science 337(6092), 2012, 303-305.
Kim, et al., "PEGylated TNF-related apoptosis-inducing ligand (TRAIL) analogues: Pharmacokinetics and antitumor effects", Bioconjugate Chem. 22(8), 2011, 1631-1637.
Kim, et al., "In vivo evaluation of polymeric micellar paclitaxel formulation: toxicity and efficacy", J. Controlled Rel. 72, 2001, 191-202.
Li, et al., "Cyclooxygenase-2 increased the angiogenic and metastatic potential of tumor cells", Biochem. Biophys. Res. Commun. 299, 2002, 886-890.
Maeda, et al., "The EPR effect for macromolecular drug delivery to solid tumors: Improvement of tumor uptake, lowering of systemic toxicity, and distinct tumor imaging in vivo", Adv. Drug Del. Rev. 65(1), 2013, 71-79.

(Continued)

*Primary Examiner* — Jake M Vu
(74) *Attorney, Agent, or Firm* — Meunier Carlin & Curfman LLC

(57) ABSTRACT

Disclosed are compositions that comprise a cyclooxygenase-2-selective therapeutic and/or diagnostic agent having a therapeutic and/or diagnostic agent conjugated to a NSAID drug; and a ROS-responsive nanoparticle. Methods of making and using these compositions for drug encapsulation and delivery are also disclosed.

13 Claims, 8 Drawing Sheets

(56) References Cited

OTHER PUBLICATIONS

Maier, et al., "Cyclooxygenase-2 (COX-2)-dependent and -independent anticarcinogenic effects of celecoxib in human colon carcinoma cells", Biochem. Pharm. 67, 2004, 1469-1474.
Meglio, et al., "Amelioration of Acute Inflammation by Systemic Administration of a Cell-Permeable Peptide Inhibitor of NF-kB Activation", Arthritis Rheumat. 52, 2005, 951-958.
Nakanishi, et al., "Development of the polymer micelle carrier system for Doxorubicin", J. Controlled Rel. 74, 2001, 295-302.
Napoli, et al., "Oxidation-responsive polymeric vesicles", Nature Materials 3(3), 2004, 183-189.
Nukulova, "Folate-decorated nanogels for targeted therapy of ovarian cancer", Biomaterials 32, 2011, 5417-5426.
Papahadjopoulos, et al., "Sterically stabilized liposomes: Improvements in pharmacokinetics and antitumor therapeutic efficacy", Proc. Natl. Acad. Sci. USA 88, 1991, 11460-11464.
Perry, et al., "PEGylated PRINT Nanoparticles: The impact of PEG density on protein binding, macrophage association, biodistribution, and pharmacokinetics", Nano Letters. 12, 2012, 5304-5310.
Poole, et al., "ROS-responsive microspheres for on demand antioxidant therapy in a model of diabetic peripheral arterial disease", Biomaterials 41, 2015, 166-175.
Reddy, et al., "In vivo targeting of dendritic cells in lymph nodes with poly(propylene sulfide) nanoparticles", J. Controlled Rel. 112, 2006;26-34.
Smith, et al., "Prostaglandin endoperoxide H synthases (cyclooxygenases)-1 and -2", J. Biol. Chem. 271(52), 1996, 33157-33160.
Soo Choi, et al., "Renal clearance of quantum dots", Nat. Biotech. 25(10), 2007, 1165-1170.
Sugahara, et al., "Tissue-penetrating delivery of compounds and nanoparticles into tumors", Cancer Cell 16, 2009, 510-520.
Taketo, et al., "Cyclooxygenase-2 Inhibitors in Tumorigenesis", J. Natl. Cancer Inst. 90, 1998, 1609-1620 Part I and II.
Torchilin, "Tumor delivery of macromolecular drugs based on the EPR effect", Adv. Drug Del. Rev. 63(3), 2010, 131-135.
Uchino, et al., "Cisplatin-incorporating polymeric micelles (NC-6004) can reduce nephrotoxicity and neurotoxicity of cisplatin in rats", British Journal of Cancer 93, 2005, 678-687.
Uddin, et al., "Selective Visualization of Cyclooxygenase-2 in Inflammation and Cancer by Targeted Fluorescent Imaging Agents", Cancer Res. 70, 2012, 3618-3627.
Uddin, et al., "Fluorocoxib A loaded nanoparticles enable targeted visualization of cyclooxygenase-2 in inflammation and cancer", Biomaterials 92, 2016, 71-80.
Vane, et al., "Inhibition of prostaglandin synthesis as a mechanism of action for aspirin-like drugs", Nat. New Biol. 231, 1971, 232-235.
Velluto, et al., "PEG-b-PPS diblock copolymer aggregates for hydrophobic drug solubilization and release: cyclosporin A as an example", Mol. Pharm. 5, 2008;632-642.
Winterbourn, "Reconciling the chemistry and biology of reactive oxygen species", Nat. Chem. Biol. 4(5), 2008, 278-286.
Yamamoto, et al., "Long-circulating poly(ethylene glycol)-poly(D,L-lactide) block copolymer micelles with modulated surface charge", J. Controlled Rel. 77(1-2), 2001, 27-38.

\* cited by examiner

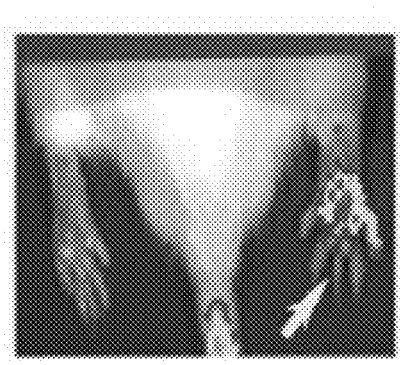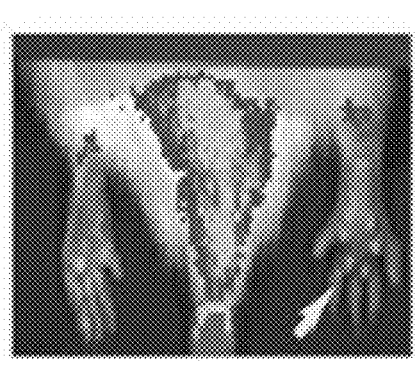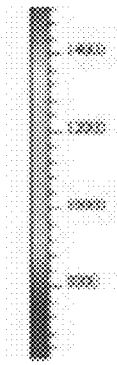
FIG. 2A  FIG. 2B
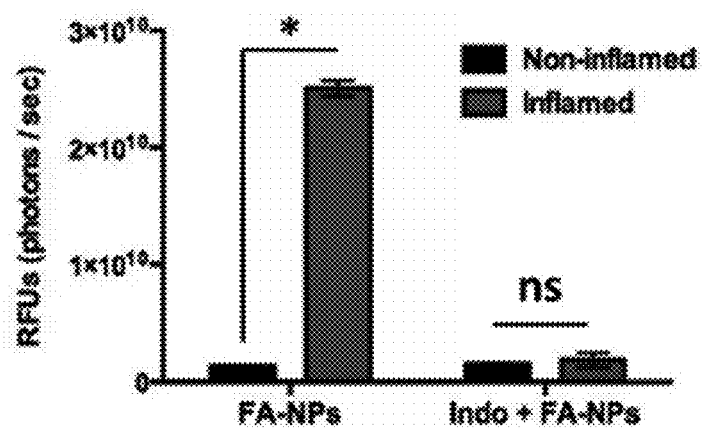
FIG. 2C

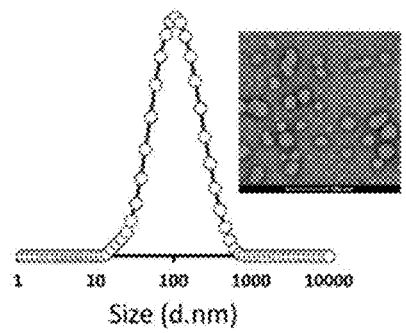
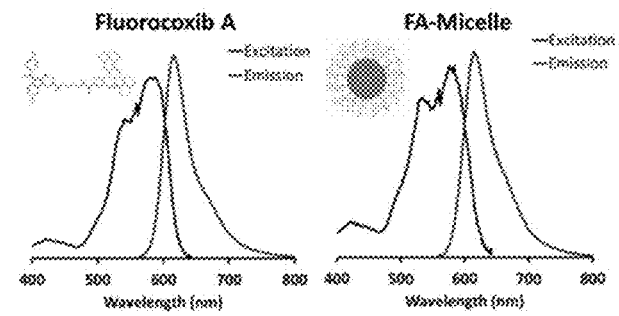
FIG. 4A　　　　　　　　　　　FIG. 4B
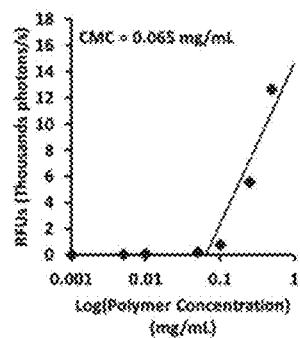
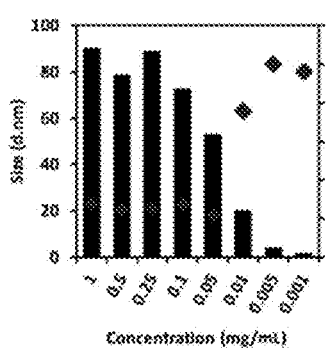
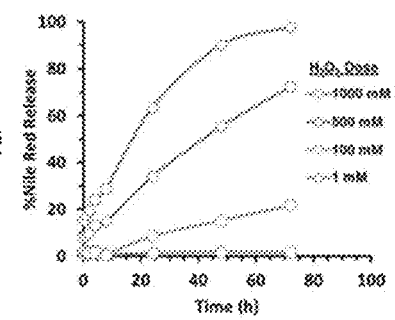
FIG. 4C　　　　FIG. 4D
FIG. 4E

FLUOROCOXIB A LOADING INTO ROS-RESPONSIVE NANOPARTICLES

CROSS REFERENCE TO RELATED APPLICATIONS

This application claims the benefit of priority to U.S. Provisional Application 62/191,367, filed Jul. 11, 2015, which is incorporated by referenced herein in its entirety.

ACKNOWLEDGMENT OF GOVERNMENT SUPPORT

This invention was made with government support under grant nos. CA89450 and CA136465 awarded by the National Institutes of Health. The government has certain rights in the invention.

BACKGROUND

Cyclooxygenases (COXs) are important biological mediators of inflammation that catalyze the biotransformation of arachidonic acid into prostaglandins and thromboxane (Vane, J. R. *Nat. New Biol.* 1971, 231:232-235). Most normal tissues express the COX-1 isoform, which performs housekeeping functions, such as maintenance of vascular tone, control of hemostasis, and cytoprotection of the gastric mucosa (Smith, W. L. et al. *J. Biol. Chem.* 1996, 271:33157-33160). In contrast, the inducible COX-2 isoform is overexpressed in inflammation, where it modulates edema and pain, and in neoplastic diseases, where it mediates tumor growth and potentiates metastasis (Li, G. et al. *Biochem. Biophys. Res. Commun.* 2002, 299:886-890). Overexpression of COX-2 is an early event of carcinogenesis, and it plays a vital role in cancer progression (Taketo, M. M. *J. Natl. Cancer Inst.* 1998, 90:1609). Moreover, COX-2 inhibitors have been shown to be effective adjuvant chemotherapeutic agents in some cancers (Gupta, R. A et al. *Natl. Cancer Inst.* 2002, 94:406-1620; Maier, T. J. et al. *Biochem. Pharmacol.* 2004, 67:1469-1474). Therefore, COX-2 is an ideal candidate for targeted visualization of inflammation and cancer.

Fluorocoxib A (FA), a fluorescent 5-carboxy-X-rhodamine-(5-ROX)-labeled COX-2-selective inhibitor, has been explored to visualize COX-2 in inflamed or cancerous tissues. Application of FA to detect COX-2 in the setting of inflammation and cancer (Uddin, M. J. et al. *J. Cancer Res.* 2010, 70:3618-3627) suggests that it may be a valuable clinical tool in these settings. However, attempts to translate it to the clinic have been hampered by its lack of solubility in aqueous solutions appropriate for human administration. All previous administrations of FA have been in 100% dimethyl sulfoxide (DMSO) or a mixed solvent consisting of DMSO (16%)/ethanol (33%)/propylene glycol (17%)/warm sterile saline (34%, 37.5° C.), that are not appropriate for human applications, especially by i.v. administration. In fact, there are many promising small molecule drugs and imaging agents, such as FA, that suffer from poor pharmacokinetics and lack of distribution to target tissues due to their hydrophobicity and/or rapid renal clearance due to low molecular weight. So what are needed are new formulations for FA, and other drug and imaging agents, which can overcome solubility challenges. The compositions and methods disclosed herein address these and other needs.

SUMMARY

Disclosed are compositions and methods for making and using the disclosed compositions. In a further aspect, disclosed are compositions that comprise a cyclooxygenase-2-selective therapeutic and/or diagnostic agent having a therapeutic and/or diagnostic agent conjugated to a NSAID drug; and a ROS-responsive nanoparticle. Methods of making and using these compositions for drug encapsulation and delivery are also disclosed.

Additional advantages of the disclosed subject matter will be set forth in part in the description that follows and the Figures, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIGS. 2A through 2C display in vivo imaging of inflammation. Sprague Dawley rats with carrageenan-induced inflammation in their right hind footpads were dosed with micelle 6 (1 mg/kg FA, i.p.) and imaged at 3 h post-injection in a Xenogen IVIS200 optical imaging instrument. FIG. 2A is an image of rat injected with micelle 6. FIG. 2B is an image of rat injected with competitive COX-binding molecule indomethacin (2 mg/kg) 1 h prior to micelle 6 injection. FIG. 2C is a quantification of signal in images of inflamed (carrageenan injected) versus non inflamed footpads with and without indomethacin pretreatment by image analysis by AMIDE software (n=8, p<0.002).

FIG. 3D is a fluorescence image of 1483 HNSCC tumor-bearing mice injected with micelle 6. FIG. 3E is a fluorescence image of 1483 HNSCC tumor-bearing mice injected with indomethacin 1 h prior to micelle 6 injection. FIG. 3F is a quantification by image analysis by AMIDE software (n=10, p=0.003). FIG. 3G is a fluorescent image of major organs of 1483 HNSCC tumor-bearing mice after micelle 6 injection and organ excision (n=9, p<0.004). FIG. 3H is an ex vivo quantitative image analysis by AMIDE software showing high signal-to-noise in targeted tumor tissues (n=3, p<0.01).

FIGS. 4A through 4E display the physicochemical characterization of micelle 6. FIG. 4A shows DLS and TEM size characterization of micelle 6. FIG. 4B shows fluorescent excitation/emission spectra of FA and FA-NPs. FIG. 4C shows CMC measurement by Nile Red assay and by DLS size and morphological changes. FIG. 4D shows hydrogen peroxide-dependent release of FA from FA-NPs. FIG. 4E is a table of PPS-b-POEGA polymer characterization values, nanoparticle size and surface charge, and drug loading.

FIG. 8A contains graphs showing serum chemical markers of liver (ALT and AST) and kidney (BUN) toxicity measured 24 h after i.v. administration of saline, 1 mg/kg, 10 mg/kg, or 20 mg/kg FA-NPs (FA dose). FIG. 8B shows H&E sections of liver and kidney at 20× magnification.

DETAILED DESCRIPTION

Figure 1:
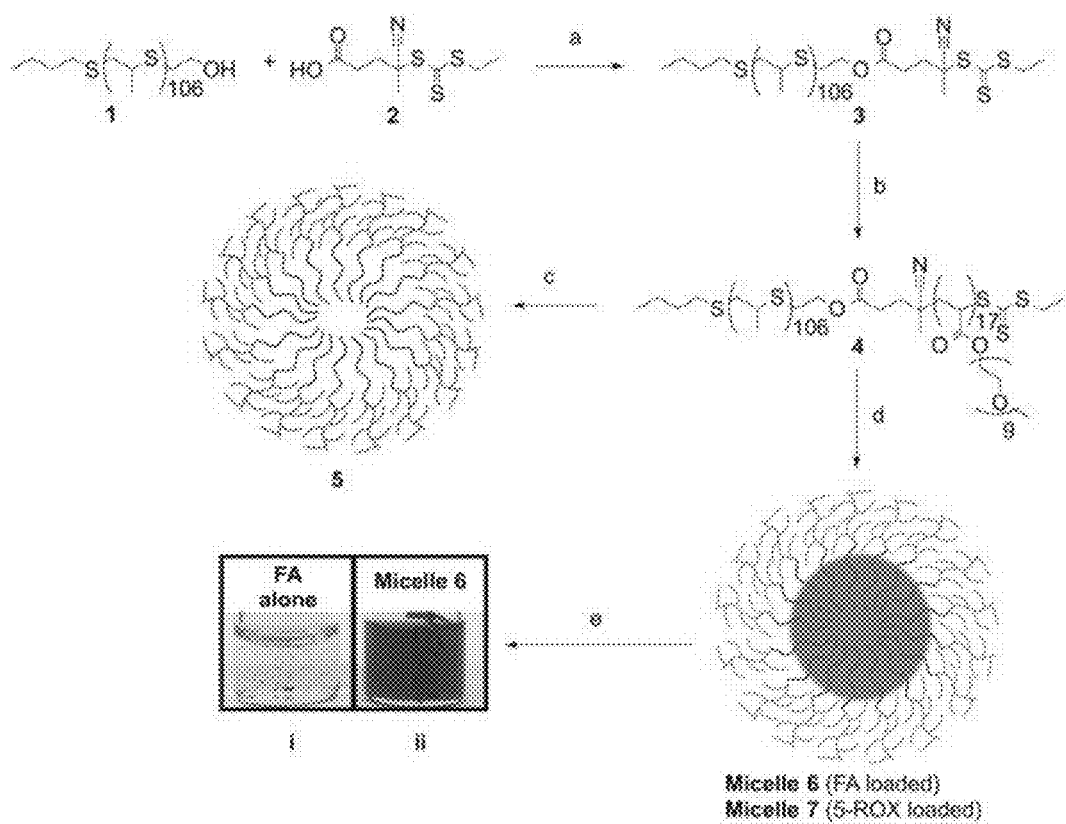
FIG. 1 displays the synthesis of $PPS_{106}$-b-$POEGA_{17}$ and FA-$PPS_{106}$-b-$POEGA_{17}$. The conditions are: (a) DCC, DMAP, $CH_2Cl_2$ 25° C., 24 h; (b) POEGA, AIBN, $(CH_2)_4O_2$ 70° C., 24 h; (c) $CH_2Cl_2$, PBS, 25° C., 24 h.; (d) FA or 5-ROX, $CH_2Cl_2$, PBS, 25° C., 24 h; (e) solubilization of FA alone or micelle 6 (referred to herein as "FA-NPs") in PBS—(i) Fluorocoxib A (1 mg/mL) and (ii) micelle 6 (1 mg/mL FA).

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth or inflammation). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as—$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula—C(O)H. Throughout this specification "C(O)" or "CO" is a short hand notation for C=O, which is also referred to herein as a "carbonyl."

The terms "amine" or "amino" as used herein are represented by the formula—$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is—C(O) $NZ^1Z^2$.

The term "carboxylic acid" as used herein is represented by the formula—C(O)OH. A "carboxylate" or "carboxyl" group as used herein is represented by the formula—C(O) $O^-$.

The term "ester" as used herein is represented by the formula—OC(O)$Z^1$ or—C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula—OH.

The term "nitro" as used herein is represented by the formula—$NO_2$.

The term "silyl" as used herein is represented by the formula—Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula—S(O)$_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula—S(O)$_2$NH—.

The term "thiol" as used herein is represented by the formula—SH.

The term "thio" as used herein is represented by the formula—S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compositions

Polymeric nanoparticles provide a promising approach for solubilizing and altering the pharmacokinetics of small molecules in vivo (Hubbel, J. A. et al. *Sci.* 2012, 337(6092): 303-305; Danhier, F. et al. *J. Controlled Rel.* 2010, 148(2): 135-146). For example, amphiphilic diblock polymers can be designed to self-assemble into micellar nanoparticles that enable solubilization of hydrophobic compounds by sequestering them into a hydrophobic core surrounded by a hydrated corona. Utilization of inert, hydrophilic macromolecules such as poly(ethylene glycol) (PEG) to form the corona enhances nanoparticle stealth, reducing opsonization and rate of clearance by the mononuclear phagocyte system (MPS) (SooChoi, H. et al. *Nat. Biotech.* 2007, 25(10):1165-1170; Yamamoto, Y. et al. *J. Controlled Rel.* 2001, 77(1-2): 27-38; Kim, T. H. et al. *Bioconjugate Chem.* 2011, 22(8): 1631-1637; Papahadjopoulos, D. et al. *Proc. Natl. Acad. Sci. USA* 1991, 88(24):11460-11464). Ideal nanoparticle formulations have a hydrodynamic diameter greater than ~10 nm, which avoids rapid renal clearance, and fall into a size range (approximately 20-200 nm) that enhances passive targeting to cancer and inflammation by the enhanced permeation and retention (EPR) effect (Torchilin, V. *Adv. Drug Del. Rev.* 2011, 63(3):131-135; Maeda, H. et al. *Adv. Drug Del. Rev.* 2013, 65(1):71-79). Material responsiveness to environmental cues, such as changes in pH and reactive oxygen species (ROS), can then be leveraged to trigger cargo release within these tissues (Winterbourn, C. C. *Nat. Chem. Biol.* 2008, 4(5):278-286; Napoli, A. et al. *Nat Mater* 2004, 3(3):183-189; Gao, W. et al. *Mol. Pharmaceutics* 2010, 7(6):1913-1920).

Disclosed herein is in vivo validation of a diblock polymer that self-assembles into water-soluble micellar nanoparticles that efficiently encapsulate/solubilize FA, or other molecules, and that release their cargo in response to ROS. This diblock polymer, poly(propylene sulfide)$_{106}$-b-poly [oligo(ethylene glycol)$_9$ methyl ether acrylate]$_{17}$ (PPS$_{106}$-b-POEGA$_{17}$), was synthesized by a combination of anionic and reversible addition-fragmentation chain-transfer (RAFT) polymerization (FIG. 1).

The hydrophobic PPS block forms the nanoparticle core, which allows for efficient encapsulation of FA. Further, PPS undergoes a phase transition from hydrophobic to hydrophilic (propylene sulfide to propylene sulfoxides and sulphones) in response to ROS, preferentially releasing cargo in response to high levels of oxidative stress, such as at sites of inflammation (Napoli Id.; Gupta, M. K. et al. *J. Controlled Rel.* 2012, 162(3):591-598; Gupta, M. K. et al. *J. Am. Chem. Soc.* 2014, 136(42):14896-14902). COX-2 overexpression and increased ROS-production are naturally concomitant phenomenon, which supports the mechanism of PPS for these applications. The POEGA block forms a brush-like arrangement of molecules of 9 repeating units of ethylene glycol grafted from a hydrocarbon backbone. More of less repeating can be used however. Recent studies have shown that POEGA's brush-like surface architecture enhances MPS stealth and overall circulation time over linear PEG (Gao W. et al. *Proc. Natl. Acad. Sci.* 2009, 106:15231-15236; Gao W. et al. *Proc. Natl. Acad. Sci.* 2010, 107:16432-16437; Perry J. L. et al. *Nano Letters.* 2012, 12:5304-5310). This is the first attempt at utilizing the brush-like POEGA architecture within a ROS-responsive, PPS nanoparticle.

The major limitation for clinical translation of FA is its poor water solubility. The disclosed micelle-based composition solubilizes FA by encapsulation into ROS-responsive micelles, thus overcoming this barrier to translation. The multi-stage targeted reagent, e.g., FA-PPS$_{106}$-b-POEGA$_{17}$, is capable of precise visualization of COX-2 in animal models of inflammation and cancer. Micelle 6 (also referred to herein as "FA-NPs") solubilizes FA and delivers it effectively to pathological sites in vivo, where it can selectively bind COX-2. High affinity FA binding to COX-2 causes a robust and stable signal to accumulate and be retained at the target site, whereas the fluorescent signal does not accumulate in control tissues or if the binding site of COX-2 is blocked. Nanocarriers developed as in vivo theranostics often suffer from rapid MPS removal in organs such as the liver and spleen, and the percent injected dose that reaches tumors is often significantly less than the distribution to the liver. Micelle 6 shows an unprecedented level of selectivity of uptake in inflammatory tissue and tumors (2-fold above liver) compared to the surrounding normal tissues, without normalization to tissue weight. The target tissue specificity declines when the COX-2 active site is pre-blocked by indomethacin, confirming that micelle 6 releases FA for molecular binding to COX-2 in vivo. Thus, micelle 6 represents a uniquely effective reagent for FA solubilization and targeted clinical detection of tissues expressing elevated levels of COX-2 in settings amenable to fluorescent measurements (superficial imaging and/or endoscopy).

The compositions disclosed herein comprise a cyclooxygenase-2-selective therapeutic and/or diagnostic agent having a therapeutic and/or diagnostic agent conjugated to a NSAID drug; and a ROS-responsive nanoparticle based on polypropylene sulfide (PPS) and/or polycaprolactone (PCL). Examples of suitable cyclooxygenase-2-selective therapeutic and/or diagnostic agent are disclosed in U.S. Pat. Nos. 8,865,130, 8,143,302, 7,736,624, which are hereby incorporated by reference in their entireties for their teachings of compositions for diagnostic and therapeutic targeting of COX-2, and methods of using and making such compositions.

NSAID Drugs

In some examples, the NSAID drug is selected from the group consisting of fenamic acids, indoles, phenylalkanoic acids, phenylacetic acids, coxibs, pharmaceutically acceptable salts thereof, and combinations thereof. In some examples, the NSAID drug is selected from the group consisting of aspirin, o-(acetoxyphenyl)hept-2-ynyl sulfide (APHS), indomethacin, 6-methoxy-α-methyl-2-naphthylacetic acid, meclofenamic acid, 5,8,11,14-eicosatetraynoic acid (ETYA), diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomepirac, celecoxib, pharmaceutically acceptable salts thereof, and combinations thereof. In other examples, the NSAID drug is selected from the group consisting of indomethacin, celecoxib, pharmaceutically acceptable salts thereof, and combinations thereof.

Diagnostic Agent

In still other examples, the cyclooxygenase-2-selective therapeutic and/or diagnostic agent has the diagnostic agent and the diagnostic agent comprises a fluorescent molecule selected from the group consisting of a fluorophore, a cyanine dye, and a near infrared (NIR) dye. In still other examples, the diagnostic agent is 6-carboxy-X-rhodamine, Cy5, Cy5.5, and Cy7, NIR641, NIR664, NIR700, and NIR782. In certain examples, the diagnostic agent is 5-carboxy-X-rhodamine. In specific examples, the cyclooxygenase-2-selective therapeutic is:

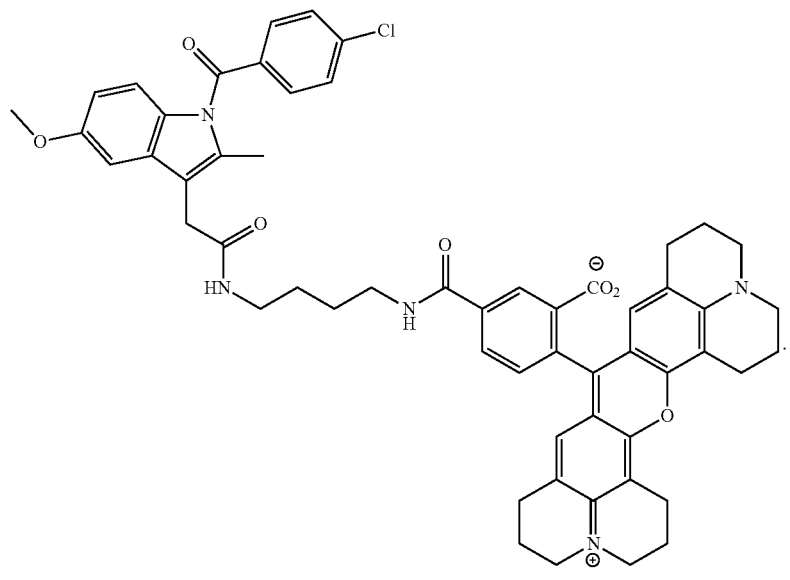

Fluorocoxib A (FA)

Further examples of suitable detectable agents include, but are not limited to, a UV-Vis label, a near-infrared label, a luminescent group, a phosphorescent group, a magnetic spin resonance label, a photosensitizer, a photocleavable moiety, a chelating center, a heavy atom, a radioactive isotope, a isotope detectable spin resonance label, a paramagnetic moiety, a chromophore, or any combination thereof. In some embodiment, the label is detectable without the addition of further reagents.

In some examples, the detectable agent can contain a luminophore such as a fluorescent label or near-infrared label. Examples of suitable luminophores include, but are not limited to, metal porphyrins; benzoporphyrins; azabenzoporphyrine; napthoporphyrin; phthalocyanine; polycyclic aromatic hydrocarbons such as perylene, perylene diimine, pyrenes; azo dyes; xanthene dyes; boron dipyoromethene, aza-boron dipyoromethene, cyanine dyes, metal-ligand complex such as bipyridine, bipyridyls, phenanthroline, coumarin, and acetylacetonates of ruthenium and iridium; acridine, oxazine derivatives such as benzophenoxazine; aza-annulene, squaraine; 8-hydroxyquinoline, polymethines, luminescent producing nanoparticle, such as quantum dots, nanocrystals; carbostyril; terbium complex; inorganic phosphor; ionophore such as crown ethers affiliated or derivatized dyes; or combinations thereof. Specific examples of suitable luminophores include, but are not limited to, Pd (II) octaethylporphyrin; Pt (II)-octaethylporphyrin; Pd (II) tetraphenylporphyrin; Pt (II) tetraphenylporphyrin; Pd (II) meso-tetraphenylporphyrin tetrabenzoporphine; Pt (II) meso-trapheny metrylbenzoporphyrin; Pd (II) octaethylporphyrin ketone; Pt (II) octaethylporphyrin ketone; Pd (II) meso-tetra(pentafluorophenyl)porphyrin; Pt (II) meso-tetra (pentafluorophenyl) porphyrin; Ru (II) tris (4,7-diphenyl-1,10-phenanthroline) (Ru $(dpp)_3$); Ru (II) tris (1,10-phenanthroline) $(Ru(phen)_3)$, tris(2,2'-bipyridine)ruthenium (II) chloride hexahydrate $(Ru(bpy)_3)$; erythrosine B; fluorescein; eosin; iridium (III) ((N-methyl-benzimidazol-2-yl)-7-(diethylamino)-coumarin)); indium (III) ((benzothiazol-2-yl)-7-(diethylamino)-coumarin))-2-(acetylacetonate); Lumogen dyes; Macroflex fluorescent red; Macrolex fluorescent yellow; Texas Red; rhodamine B; rhodamine 6G; sulfur rhodamine; m-cresol; thymol blue; xylenol blue; cresol red; chlorophenol blue; bromocresol green; bromcresol red; bromothymol blue; Cy2; a Cy3; a Cy5; a Cy5.5; Cy7; 4-nitrophenol; alizarin; phenolphthalein; o-cresolphtalein; chlorophenol red; calmagite; bromo-xylenol; phenol red; neutral red; nitrazine; 3,4,5,6-tetrabromphenolphtalein; congo red; fluorescein; eosin; 2',7'-dichlorofluorescein; 5(6)-carboxy-fluorescein; carboxynaphtofluorescein; 8-hydroxypyrene-1,3,6-trisulfonic acid; semi-naphthorhodafluor; semi-naphthofluorescein; tris (4,7-diphenyl-1,10-phenanthroline) ruthenium (II) dichloride; (4,7-diphenyl-1,10-phenanthroline) ruthenium (II) tetraphenylboron; platinum (II) octaethylporphyin; dialkylcarbocyanine; and dioctadecylcycloxacarbocyanine; derivatives or combinations thereof.

The detectable agent can contain a radiolabel, also referred to herein as radioisotope. The radiolabel can also be a therapeutic moiety, i.e., a radiolabel comprising a therapeutic radionuclide such as, $^{90}Y$ or $^{177}Lu$. Other examples of suitable radiolabels include, but are not limited to, metal $^{18}F$, $^{64}Cu$, $^{67}Cu$, $^{89}Zr$, $^{111}In$, $^{124}I$, $^{123}I$, and $^{99m}Tc$. In some embodiments, the radiolabel can be chelated by a macrocyclic molecule. Examples of such macrocyclic molecules include, but are not limited to, 2,2',2''-(10-(2-((2,5-dioxopyrrolidin-1-yl)oxy)-2-oxoethyl)-1,4,7,10-tetraazacyclododecane-1,4,7-triyl)triacetic acid (DOTA)-based chelators, diethylene triamine pentaacetic acid (DTPA)-based chelators, and a derivative or a combination thereof.

ROS-responsive nanoparticle

In some instances, the nanoparticles (e.g., micelles) are formed from a plurality of the diblock copolymers which self-associate through the interactions of the hydrophobic blocks (e.g., core blocks) of the block copolymers, and/or are stabilized through their hydrophobic interactions in the core. In certain examples, the nanoparticle is a micelle. In yet further examples, the micelle has a size of approximately 10 nm to about 200 nm, about 10 nm to about 100 nm, or about 30-80 nm. Particle size can be determined in any manner, including, but not limited to, by gel permeation chromatography (GPC), dynamic light scattering (DLS), electron microscopy techniques (e.g., TEM), and other methods. The micelles provided herein are prepared by spontaneous self-assembly of the polymers described herein. In certain embodiments, the polymers described herein assemble into the nanoparticle provided herein (a) upon dilution of a solution of the polymer in water-miscible organic solvent into aqueous media, or (b) being dissolved directly in an aqueous solution.

The nanoparticle (e.g., micelles) are stable to dilution in an aqueous solution. In specific embodiments, the nanoparticle (e.g., micelles) are stable to dilution at about neutral pH with a critical stability concentration (e.g., a critical micelle concentration (CMC)) of approximately 50 to approximately 100 µg/mL, or approximately 10 to approximately 50 µg/mL, less than 10 µg/mL, less than 5 µg/mL, less than 2 µg/mL, less than 0.5 µg/mL, or less than 0.1 µg/mL. As used herein, "destabilization of a micelle" means that the polymeric chains forming a micelle at least partially disaggregate, structurally alter (e.g., expand in size and/or change shape), and/or may form amorphous supramolecular structures (e.g., non-micellic supramolecular structures). The terms critical stability concentration (CSC) and critical micelle concentration (CMC) are used interchangeably herein.

In specific embodiments, the nanoparticle (e.g., micelle) comprises a plurality of block copolymers forming a shell and a core of the nanoparticle (e.g., a micelle). In certain embodiments, the shell and/or shell block is hydrophilic and/or charged (e.g., cationic, polycationic, or zwitterionic). In some specific embodiments, the shell and/or shell block comprises a net positive charge. In other embodiments, the shell and/or shell block is hydrophilic and neutral. In some embodiments, the core and/or core block is hydrophobic and/or comprises hydrophobic groups, moieties, monomeric units, species, or the like. In specific embodiments, the hydrophobic core and/or core block comprise a plurality of hydrophobic groups, moieties, monomeric units, species, or the like and a plurality of chargeable species or monomeric units. In more specific embodiments, the plurality of chargeable monomeric units or species comprises a plurality of anionic chargeable monomeric units or species. In still more specific embodiments, the plurality of chargeable monomeric units or species comprises a plurality of cationic and a plurality of anionic chargeable monomeric units or species. In some embodiments, the block copolymers each have (1) a hydrophilic, charged block (e.g., cationic or polycationic) or neutral block, forming the shell of the nanoparticle (e.g., micelle), (2) a hydrophobic block, and optionally (3) a plurality of anionic chargeable species, and are membrane destabilizing (e.g., become membrane destabilizating in a pH dependent manner). In certain embodiments, the hydrophobic core and/or core block optionally comprise spacer monomeric units which may or may not comprise hydrophobic groups, chargeable groups, or a combination thereof. In some embodiments, a polymer block forming or present in the core of the nanoparticle (e.g., micelle) (e.g., one or more core block of the copolymer) is chargeable (e.g., contains cationic and/or anionic species at a physiological pH). As used herein, chargeable species and/or monomeric units include species and monomeric units in both the charged and non-charged states. In some instances, the nanoparticles (e.g., micelles) provided herein are formed from a plurality of block copolymers which self-associate. In certain instances, the self-association occurs through the interactions of the hydrophobic blocks of the block copolymers and the resulting nanoparticle (e.g., micelles) are stabilized through hydrophobic interactions of the hydrophobic blocks present in the core of the nanoparticle.

The ROS-responsive nanoparticle comprises a plurality of diblock copolymers. The diblock copolymer comprises a poly(propylene sulfide) or polycaprolactone (PCL) block. The poly(propylene sulfide) block can have from 80 to 100 propylene sulfide residues. The polycaprolactone block can have from 80 to 100 ester moieties. The diblock copolymer can comprise a poly(oligo(ethylene glycol) methyl ether acrylate] block having from 2 to 50 oligo(ethylene glycol) methyl ether acrylate residues. In a specific example, the ROS-responsive nanoparticle can comprise a plurality of poly(propylene sulfide)$_{106}$-b-poly[oligo(ethylene glycol)$_9$ methyl ether acrylate]$_{17}$ copolymers.

Pharmaceutical Compositions

The compounds described herein can be formulated for enteral, parenteral, topical, or pulmonary administration. The compounds can be combined with one or more pharmaceutically acceptable carriers and/or excipients that are considered safe and effective and can be administered to an individual without causing undesirable biological side effects or unwanted interactions. The carrier is all components present in the pharmaceutical formulation other than the active ingredient or ingredients.

The compounds described herein can be formulated for parenteral administration. "Parenteral administration", as used herein, means administration by any method other than through the digestive tract or non-invasive topical or regional routes. For example, parenteral administration can include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques known in the art. Typically, such compositions can be prepared as injectable formulations, for example, solutions or suspensions; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

Solutions and dispersions of the active compounds can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer™ 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the active agent(s).

The formulation is typically buffered to a pH of 3-8 for parenteral administration. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above.

For parenteral administration, the compound can be incorporated into microparticles, nanoparticles, or combinations thereof. For example, the compound can be incorporated into polymeric microparticles.

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations can be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Suitable dosage forms for topical administration include creams, ointments, salves, sprays, gels, lotions, emulsions, and transdermal patches. The formulation can be formulated for transmucosal, transepithelial, transendothelial, or transdermal administration. The compounds can also be formulated for intranasal delivery, pulmonary delivery, or inhalation. The compositions can further contain one or more chemical penetration enhancers, membrane permeability agents, membrane transport agents, emollients, surfactants, stabilizers, and combination thereof.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocyclic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorbtion occurs. The alveoli are covered by a thin epithelium without cilia or a mucus blanket and secrete surfactant phospholipids. Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

The compounds described herein can be co-administered with one or more additional active agents, such as diagnostic agents, therapeutic agents, and/or prophylactic agents.

Methods of Making

Anionic polymerization of propylene sulfide was done using 1-butanethiol as an initiator in the presence of 1,8-diazabicyclo[5.4.0]undec-7-ene (DBU). The propagation of the PPS block was quenched by the addition of 2-iodoethanol in order to introduce hydroxyl groups at one terminus of the PPS chains. Using a carbodiimide coupling strategy, poly(propylene sulfide)ethan-1-ol ($PPS_{106}$-OH, 1) was conjugated with 4-cyano-4-(ethylsulfanylthiocarbonyl) sulfanylpentanoic acid (ECT, 2) (Convertine, A. J. et al. *J. Controlled Rel.* 2009, 133(3):221-229) to form the poly (propylene sulfide)-ECT ($PPS_{106}$-ECT RAFT macro-CTA, 3). The macro-CTA was then used for the RAFT polymerization of oligo(ethylene glycol) methyl ether acrylate to afford PPS-b-POEGA (4). The $PPS_{106}$-b-$POEGA_{17}$ (5) and FA-$PPS_{106}$-b-$POEGA_{17}$ (6) micelles were formed by self-assembly in aqueous medium by the solvent evaporation method in the absence of fluorophore (5), or in the presence of either FA (6) or 5-ROX (7) (FIG. 1). The average FA loading was ~0.062 (wt drug/wt polymer), and encapsulation efficiency was ~62%. Micelle 6 is monodispersed with a diameter centered around 110 nm as determined by dynamic light scattering (DLS) and transmission electron microscopy (TEM) (FIG. 4), and the zeta potential is approximately neutral (−1.51±0.6 mV) (FIG. 4). The FA showed a lack of solubility in water (precipitates visible in an otherwise clear aqueous solution), whereas the micelle 6-encapsulated FA formed a solution with a deep purple color and without any apparent turbidity, suggesting stable FA colloidal solubilization by the nanoparticles (FIG. 1).

Methods of Use

The disclosed compositions can be used to deliver FA, or other molecules, to sites in vivo where COX-2 expression or overexpression occurs (e.g., sites of inflammation). The disclosed compositions can also be used to image certain sites where COX-2 expression or over expression occurs. For example, micelle 6 was evaluated in vivo using carrageenan-induced inflammation in the Sprague Dawley rat footpad. It is well documented that COX-2-derived prostaglandins are major contributors to the acute inflammation that develops 2 h after carrageenan injection into the paw in this model (Meglio, D. P. et al. *Arthritis Rheumat.* 2005, 52:951-958). The footpad model is ideal for imaging inflammation because it enables a direct comparison between the locally-inflamed footpad and the vehicle-injected non-inflamed contralateral footpad; the latter does not express high levels of COX-2. The Sprague Dawley rat hind footpad was injected with 100 µL 1% carrageenan followed by micelle 6 (1 mg/kg FA, intraperitoneal (i.p.)) at 2 h post-carrageenan. Animals were imaged 3 h later in a Xenogen IVIS 200 (Cy5.5 filter, 1.5 cm depth, 1 sec). Micelle 6 targeted the inflamed footpad with an average 10-fold increase in fluorescence over that of the contralateral control footpad (FIGS. 2A and 2B). Furthermore, the uptake was efficiently blocked by pretreatment with the nonselective COX inhibitor indomethacin. The results in the rat footpad inflammation model demonstrate that micelle 6 effectively targets sites of inflammation in vivo in order to visualize COX-2 in carrageenan-induced edema. The blocking study further confirms that the FA molecule is released from the nanoparticle and able to engage COX-2.

Figures 3A, 3B, 3C:
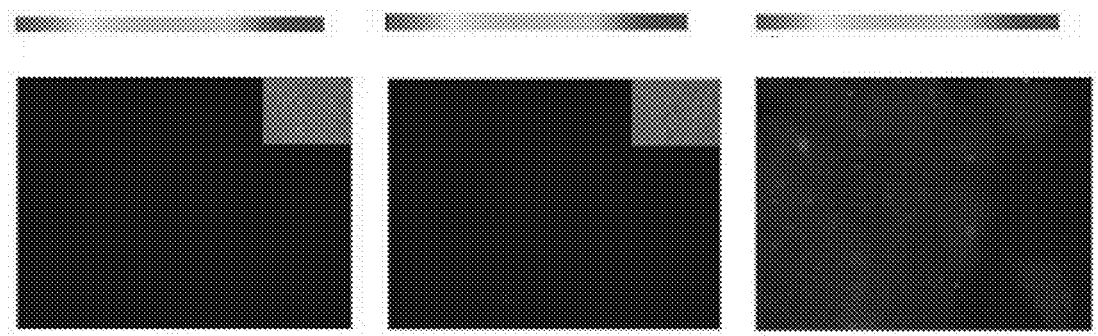
FIGS. 3A through 3H display in cellulo and in vivo imaging of 1483 HNSCC cells and tumors. 1483 HNSCC cells were treated for 50 min with (FIG. 3A) micelle 5, (FIG. 3B) micelle 7, or (FIG. 3C) micelle 6, washed, and imaged on a fluorescence microscope (Leica DM IL LED FIM) at 40× magnification. Female nude mice bearing COX-2-expressing 1483 HNSCC tumor xenografts or indomethacin-pretreated animals bearing COX-2-expressing 1483 HNSCC xenografts were dosed with micelle 6 (1 mg/kg FA, i.p.) and imaged at 4 h post-injection of probes in a Xenogen IVIS200 optical imaging instrument.

Next, micelle 6 was evaluated for targeting COX-2 in human 1483 head and neck squamous cell carcinoma (HNSCC) human cancer cells. After pre-incubation for 50 min with micelle 5, 6, or 7 (FIGS. 3A through 3C), the 1483 cells were washed, incubated for 50 min in serum-containing medium, and imaged under a fluorescence microscope. Micelle 6 was the only reagent that showed fluorescence in vitro, confirming its effective delivery of FA to COX-2-overexpressing cell types and further motivating its characterization for in vivo imaging of cancer. Moreover, the lack of fluorescence observed with micelle 7, which contains the non-binding 5-ROX, confirms that specific binding to COX-2 is required for effective visualization of COX-2-overexpressing cells.

Figures 3D, 3E, 3F:
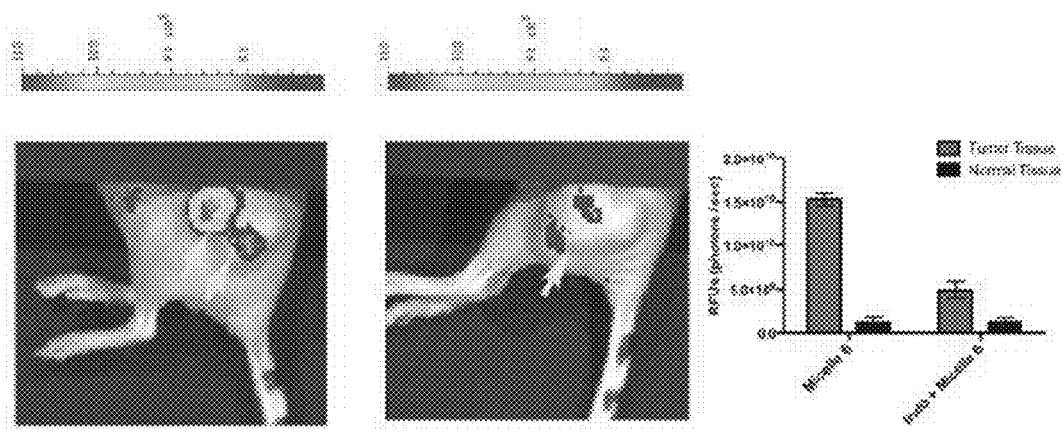

Micelle 6 was evaluated for targeting COX-2 in 1483 HNSCC tumor xenografts in vivo. Female nude mice were injected in the left flank with 1483 HNSCC cells, and the xenografts were allowed to grow to approximately 800-1000 $mm^3$. Animals were dosed by i.p. injection with micelle 6 (1 mg/kg FA), then anesthetized with 2% isoflurane for imaging. No fluorescence was observed in the tumor during the first 30 min post-injection, but signal was reproducibly detected in the COX-2-expressing 1483 tumors starting at 3.5 to 4.5 h post-injection. It was next evaluated whether fluorescence observed in the tumors was due strictly to nanoparticle accumulation within the tissue by EPR effect or also by release of the FA molecule and its binding to COX-2. To this end, nude mice with 1483 xenografts were pretreated with either DMSO or indomethacin in DMSO (2 mg/kg, i.p.) prior to micelle 6 dosing (1 mg/kg FA, i.p.). At 3 h post-injection, the DMSO-pretreated mice showed strong fluorescence in their tumors whereas the tumors of the indomethacin-pretreated mice displayed much lower fluorescence (FIGS. 3D and 3F). This observation confirms that FA retention in the tumor requires its release from micelle 6 in order for it to bind specifically with COX-2.

Figures 3G, 3H:
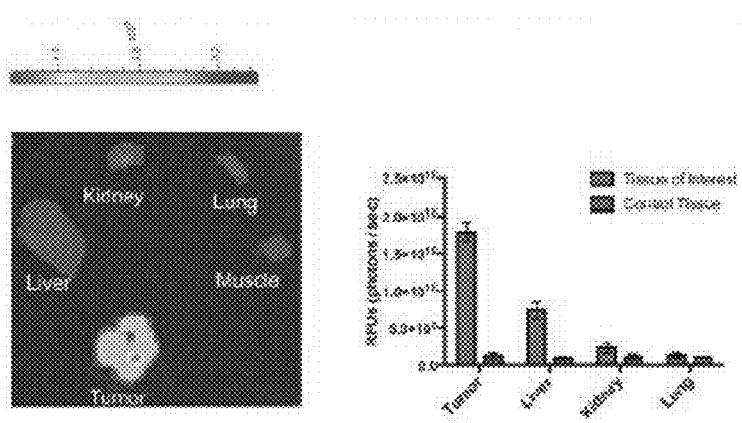

The combination of the nanoparticle-mediated EPR effect, ROS-triggered nanoparticle disassembly, and the high affinity binding of FA to COX-2 provides a unique, multi-stage mechanism for attaining unprecedentedly high uptake and signal-to-noise in COX-2-expressing tissues compared with normal tissues. To investigate the advantage of this multi-stage targeting, the biodistribution of the probe in the liver, kidney, lung, tumor, and adjacent muscle was assessed by ex vivo optical imaging of tissues from nude mice with 1483 xenografts 3 h after injection of micelle 6 (1 mg/kg FA, i.p.). Remarkably, maximal signal was documented in the tumor even without normalization to tissue weight, with tumor fluorescence 2-fold above liver fluorescence (FIGS. 3G and 3F). Due to lack of solubility of FA in PBS, it was not used as a control in these experiments. In total, these tumor biodistribution results compare favorably to nanoparticles currently in clinical trials (Kim S. C. et al. *J. Controlled Rel.*, 2001, 72:191-202; Nakanishi T. et al. *J. Controlled Rel.*, 2001, 74:295-302; Uchino H. et al. *British Journal of Cancer,* 2005, 93:678-687; Alakhov V. et al. *Colloids and Surfaces B: Biointerfaces,* 1999, 16:113-134) and to other state-of-the-art pre-clinical technologies (Cabral H. et al. *Nature Nanotechnology,* 2011, 6:815-823; Nukulova N. V. et al. *Biomaterials,* 2011, 32:5417-5426; Sugahara K. N. et al. *Cancer Cell,* 2009, 16:510-520; Bertrand N. et al. *Adv. Drug Del. Rev.,* 2014, 66:2-25).

The disclosed micellar compositions can be used to image or treat various sites associated with cancer. COX-2 is dramatically up regulated during inflammation and human cancers (Crofford L. J., et al., *J. Rheumatology* 1997, 49:15-19; DuBois R. N., et al., *J Clin Oncology* 2005, 23:254-266). In particular there is a significant unmet need for early detection of colorectal cancers. Other cancers that can be imaged or treated by the disclosed compositions are shown in Table 1.

TABLE 1

COX-2 is Overexpressed in Premalignant and Malignant Tissues

| Organ | Premalignancy | Malignancy |
|---|---|---|
| Head and neck | Leukoplakia | Squamous cell carcinoma |
| Esophagus | Barrett's esophagus | Adenocarcinoma; squamous cell carcinoma |
| Stomach | Metaplasis | Adenocarcinoma |
| Colon | Adenoma | Adenocarcinoma |
| Liver | Chronic hepetitis | Hepetocellular carcinoma |
| Biliary System | Bile duct hyperplasia | Cholangiocarcinoma; adenocarcinoma of gall bladder |
| Pancreas | Pancreatic intraepithelial neoplasia | Adenocarcinoma |
| Breast | Ductal carcinoma-in-situ | Adenocarcinoma |
| Lung | Atypical adenomatous hyperplasia | Adenocarcinoma; squamous cell carcinoma |
| Bladder | Dysplasia | Transitional cell carcinoma; squamous cell carcinoma |
| Gynecologic | Cervical intraepithelial neoplasia | Squamous cell carcinoma or adenocarcinoma of cervix; endometrial carcinoma |
| Penis | Penile intraepithelial neoplasia | Squamous cell carcinoma |
| Skin | Actinic keratoses | Squamous cell carcinoma |

Further provided herein are methods of treating or preventing cancer in a subject that comprise the administration of an effective amount a compound or composition as disclosed herein to the subject. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation. Methods of treating inflammation in a subject are further provided herein, the methods comprising administering to the subject an effective amount of a compound or composition as described herein. Optionally, the methods can further include administering a second compound or composition (e.g., an anti-inflammatory agent).

The disclosed subject matter also concerns methods for treating a subject having an oncological disorder or condition. In one embodiment, an effective amount of one or more compounds or compositions disclosed herein is administered to a subject having an oncological disorder and who is in need of treatment thereof. The disclosed methods can optionally include identifying a subject who is or can be in need of treatment of an oncological disorder. The subject can be a human or other mammal, such as a primate (monkey, chimpanzee, ape, etc.), dog, cat, cow, pig, or horse, or other animals having an oncological disorder. Means for administering and formulating compounds for administration to a subject are known in the art, examples of which are described herein. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

All chemicals were purchased from Sigma-Aldrich (Milwaukee, Wis., USA) unless otherwise noted. Propylene sulfide (PS)(>96%) was purchased from Acros Organics through Fischer Scientific (Pittsburgh, Pa., USA).

Treatment groups were statistically compared using the student's t-test, where a p-value <0.05 represents a statistically significant difference between groups. All data is represented as the arithmetic mean and standard error of the indicated samples size (n).

Synthesis of Hydroxyl End-Functionalized
Poly(Propylene Sulfide) ($PPS_{106}$-OH, 1)

Poly(propylene sulfide) was prepared by anionic polymerization of propylene sulfide using DBU/1-butanethiol as an initiator and subsequently end-capped with 2-iodoethanol to yield a terminal hydroxyl group. 1,8-Diazabicyclo[5.4.0] undec-7-ene (DBU) (6.0 mmol, 0.897 mL) was dissolved in dry tetrahydrofuran (THF) (15 mL) in a dried and nitrogen flushed 50 mL round bottom flask and degassed for 30 min before lowering the reaction temperature to 0° C. 1-Butanethiol (2.0 mmol, 0.14 mL) in THF (5 mL) was added drop wise to the flask and allowed to react for 30 min. Later, freshly distilled and degassed propylene sulfide (120 mmol, 9.387 mL) monomer was added to the reaction mixture, and the temperature was maintained at 0° C. for 2 h. The reaction was quenched by addition of 2-iodoethanol (6.0 mmol, 1.03 g) and stirred overnight at room temperature (Convertine, A. J. et al., *J. Controlled Rel.* 2009, 133(3):221). After stirring overnight, the polymer solution was filtered to remove precipitated salt and further purified by three precipitations into cold methanol before vacuum-drying to yield a colorless viscous polymer. $^1$H NMR (400 MHz; $CDCl_3$, δ): 1.3-1.4 (s, $CH_3$), 2.5-2.8 (s, —CH), 2.8-3.1 (s, $CH_2$), 3.72 (t, $CH_2$—OH). ($PPS_{106}$—OH, Mn, GPC=8,200 g/mol, PDI=1.4).

Synthesis of poly(propylene sulfide)-4-cyano-4-
(ethylsulfanylthiocarbonyl) sulfanylpentanoic acid
($PPS_{106}$-ECT RAFT macro-CTA, 3)

N,N'-Dicyclohexylcarbodiimide (DCC) (0.248 g, 1.2 mmol) was added to a solution of 4-cyano-4-(ethylsulfanylthiocarbonyl) sulfanylpentanoic acid (ECT) (2, 0.314 g, 1.2 mmol), $PPS_{106}$-0H (3.12 g, 0.4 mmol), and 4-dimethylaminopyridine (DMAP) (0.015 g, 0.12 mmol) in anhydrous dichloromethane (20 mL) at 0° C. (Nelson, C. E., et al., *ACS Nano* 2013, 7(10):8870). After stirring at room temperature for 24 h, the reaction mixture was filtered to remove precipitated dicyclohexyl urea and concentrated under vacuum. The crude reaction mixture was first purified by dialysis against dichloromethane for 24 h to remove free ECT, further purified through double precipitation into cold ethanol, and characterized by $^1$H-NMR spectroscopy. $^1$H-NMR (400 MHz; $CDCl_3$, δ): 1.35 (t, 3H, —S—$CH_2$—$CH_3$), 1.3-1.4 (s, 3H, $CH_3$), 1.85 (s-C(CN)—$CH_3$), 2.4-2.67 (m, —$CH_2$—$CH_2$—S), 2.5-2.8 (broad s, S—CH), 2.8-3.1 (broad s, 2H, $CH_2$), 3.42 (q, —S—$CH_2$—$CH_3$), 3.8 (t, —$OCH_2$—$CH_2$). ($PPS_{106}$-ECT, Mn, GPC=8,200 g/mol, PDI=1.4)

Synthesis of poly(propylene sulfide)-b-poly[oligo
(ethylene glycol) methyl ether acrylate] ($PPS_{106}$-b-
$POEGA_{17}$, 4) di-block copolymer The di-block copolymer $PPS_{106}$-b-$POEGA_{17}$ was synthesized by RAFT polymerization from a $PPS_{106}$-ECT macro-chain transfer agent (macro-CTA) using azobisisobutyronitrile (AIBN) at a 10:1 (macro-CTA:AIBN) molar ratio as the radical initiator. In a dry round bottom flask (10 mL), $PPS_{106}$-ECT (0.743 g, 0.095 mmol, Mn=8,200 Da), OEGA (1.21 mL, 2.86 mmol), and AIBN (1.56 mg, 9.5 µmol) in dioxane (5 mL) were degassed by nitrogen purging for 30 min. The reaction was allowed to proceed for 24 h at 70° C. The reaction product was dialyzed against methanol for 24 h, dried under vacuum to yield a purified, milky white polymer, and characterized by $^1$H-NMR spectroscopy. $^1$H NMR (400 MHz; $CDCl_3$, δ): 1.35 (t, 3H, —S—$CH_2$—$CH_3$), 1.3-1.4 (s, 3H, $CH_3$), 1.85 (s-C(CN)—$CH_3$), 2.4-2.67 (m, —$CH_2$—$CH_2$—S), 2.5-2.8 (broad s, S—CH), 2.8-3.1 (broad s, 2H, $CH_2$), 3.42 (q, —S—$CH_2$—$CH_3$), 3.68 (m, —$OCH_2$—$CH_2$), 3.8 (t, —$OCH_2$—$CH_2$). ($PPS_{106}$-b-$POEGA_{17}$, Mn, NMR=16,004 g/mol)

Polymer Characterization $^1$H NMR spectra were collected for all polymers in $CDCL_3$ on a Brüker 400 MHz spectrometer. Molecular weights (Mn), polydispersities (PI), and compositions were determined by either $^1$H NMR (FIG. 4) or gel permeation chromatography (GPC) (Agilent Technologies, Santa Clara, Ca, USA) using dimethylformamide (DMF)+0.1 M LiBr at 60° C. as the mobile phase through three serial Tosoh Biosciences TSKGel Alpha Columns (Tokyo, Japan). Serial dilutions (10 mg/mL-0.25 mg/mL) were scanned on a digital refractometer to determine the refractive index increment (dn/dc) of polymers in order to calculate absolute molecular weights by GPC.

Preparation and Characterization of
$PPS_{106}$-b-$POEGA_{17}$ Polymer Micelles (5)

Micelles were formed of $PPS_{106}$-b-$POEGA_{17}$ by the bulk solvent evaporation method. $PPS_{106}$-b-$POEGA_{17}$ was dissolved in dichloromethane at 10 mg/mL. Polymer solution (0.1 mL) was added dropwise to 1 mL phosphate-buffered saline (PBS) (−/−) with stirring. The solution was left stirring over night to evaporate the dichloromethane and allow for micelle formation. The micelle solutions were passed through a 0.45 µm syringe filter and used for hydrodynamic diameter (Dh) and zeta potential (ζ) measurements, employing a Malvern Zetasizer Nano-ZS (Malvern Instruments Ltd, Worcestershire, UK) equipped with a 4 mW He—Ne laser operating at λ=632.8 nm (FIG. 4). TEM samples were prepared by adding 5 µL of polymer solution to pure carbon TEM grids (Ted Pella Inc, Redding, Calif., USA), blotting dry (3 s) after 60 s, and counterstaining with 3% uranyl acetate (5 µL) for 20 s. The grids were dried overnight under vacuum prior to imaging on a FEI Tecnai Osiris microscope operating at 200 kV for TEM (FIG. 4).

Loading of Fluorocoxib A and 5-ROX into
$PPS_{106}$-b-$POEGA_{17}$ Polymer Micelles
(FA/5-ROX-$PPS_{106}$-b-$POEGA_{17}$ Micelles, 6 and 7)

FA-$PPS_{106}$-b-$POEGA_{17}$ and 5-ROX-$PPS_{106}$-b-$POEGA_{17}$ micelles were prepared via the bulk solvent evaporation method. Either FA or 5-ROX and $PPS_{106}$-b-$POEGA_{17}$ were dissolved in dichloromethane, separately. Then, solutions of either FA or 5-ROX (50 µL, 20 mg/mL) and $PPS_{106}$-b-$POEGA_{17}$ (50 µL, 200 mg/mL) were mixed together, and the resulting solution was added drop wise to 1 mL PBS (−/−) with stirring. The solution was stirred overnight to evaporate dichloromethane and provide either FA- or 5-ROX-loaded micelles. Any unloaded precipitates were removed by centrifugation followed by aspiration of the supernatant solution. The drug loading was quantified as described previously (Gupta, M. K., et al., *J. Controlled Rel.* 2012, 162(3): 591-598; Hu, P., et al., *Bioconjugate Chem.* 2012, 23(3): 438). Briefly, 50 µL of DMF was added to 50 µL aliquots of the FA-loaded micelles in order to re-dissolve micelles. Fluorescence intensity (ex: 581 nm, em: 605 nm) was measured on a TECAN Infinite F500 micro-plate reader and compared to a standard curve of FA fluorescence in 50/50 DMF/PBS (−/−).

The $PPS_{106}$-b-$POEGA_{17}$ (NPs) and FA-loaded $PPS_{106}$-b-$POEGA_{17}$(FA-NPs) micelles were formed by self-assembly in aqueous medium by the solvent evaporation method in the absence of any small molecules (NPs), or in the presence of either FA (FA-NPs) or 5-ROX (5-ROX-NPs) (FIG. 1). The 5-ROX was formulated as a fluorescent molecule control without the COX-2-specific binding component. The FA compound alone was insoluble in water (precipitates visible in an otherwise clear aqueous solution), whereas the FA-NPs formed a deep purple solution without any apparent turbidity, suggesting stable FA colloidal solubilization (FIG. 1). This represents the first fully aqueous formulation of FA, a major step toward its clinical translation. The average FA loading was ~0.063 (wt drug/wt polymer), and encapsulation efficiency was ~63%. FA-NPs have an 82.3±8.4 nm average hydrodynamic diameter as determined by DLS, and they are slightly smaller in their dehydrated form as imaged by TEM (FIG. 4A). The zeta potential is approximately neutral (−1.51±0.6 mV). FA-NPs retained the excitation/emission fluorescence spectra of FA (FIG. 4B), although micelle loading resulted in a partial quenching effect of FA which diminished its fluorescent intensity ~13-fold (data not shown). The CMC of FA-NPs was quantified as ~0.065 mg/mL using Nile Red, and this value was confirmed by concentration-dependent changes in nanoparticle size and morphology (FIG. 4C). The CMC (~0.065 mg/mL) of FA-NPs is an order of magnitude below the diluted concentration of FA-NPs within the blood initially after i.v. administration (0.5e1.0 mg/mL) at doses used within this report. FRET-based readouts and particle morphology measurements confirmed that NPs are stable and retain their cargo in the presence of serum and whole human blood. The chosen solubilization strategy using a PPS-based micelle incorporated a mechanism for preferential cargo release in response to oxidative stress. As COX-2 overexpression and ROS production are naturally connected physiologic events, release of FA is expected to be accelerated from FA-NPs in tissues which overexpress COX-2, allowing binding and retention of FA. ROS-responsiveness of NPs was confirmed by $H_2O_2$-dependent NR release at varying concentrations of $H_2O_2$. NPs had minimal drug release when no $H_2O_2$ was present, however drug cargo was released in a dose-dependent manner upon exposure to $H_2O_2$ (FIG. 4D). In sum, the physicochemical characteristics of FA-NPs (i.e. size, surface charge, drug loading, fluorescent properties, ROS degradability, and CMC) were rigorously validated and confirm that FA-NPs constitute a fully aqueous, i.v.-ready formulation of FA.

Nanoparticle Stability in the Presence of Serum and Whole Human Blood

Förster Resonance Energy Transfer- (FRET-) pair loaded-$PPS_{106}$-b-$POEGA_{17}$ NPs (FRET-NPs) were assessed for particle stability in the presence of whole human blood and serum. FRET-NPs were generated by co-loading the FRET-pair DiO (donor)/DiI (acceptor) (chosen to model FA due to high lipiphilicity) within $PPS_{106}$-b-$POEGA_{17}$ NPs and using an excitation of 480±5 nm and emissions of DiO (517±5 nm) and DiI (573±5 nm) to calculate FRET efficiency according to the following equation:

$$FRET = I_{573}/I_{517} \pm I_{573}$$

where, $I_{517}$=fluorescent intensity of 517 nm emission and $I_{573}$=fluorescent intensity of 573 nm emission. After efficient FRET was confirmed as previously established (Gupta et al., J. Control Rel. 162:591-598, 2012), the FRET-NPs (0.25 mg/mL DiO/DiI) were incubated in whole human blood or whole human blood diluted with PBS (1:1, 1:2, 1:3, and 1:5 dilutions) for 30 min. After 30 min, samples were centrifuged and plasma was monitored on a Tecan plate reader at excitation of 480±5 nm and emissions of 517±5 nm and 573±5 nm. FRET-NPs were also incubated with varying doses of fetal bovine serum (FBS; 10, 20, 30, 40, and 50%) and FRET kinetics were monitored for 180 min. FRET-NPs (0.25 mg/mL DiO/DiI) were added to 10, 20, 30, 40, and 50% serum in a 96-well plate and FRET was measured every 5 min on a Tecan plate reader at excitation of 480±5 nm and emissions of 517±5 and 573±5 nm. The percent FRET remaining was calculated by comparing the FRET at each dose of FBS to FRETNPs incubated at analogous volume percent in PBS.

To confirm that a micellar nanoparticle structure was retained in the presence of serum, $PPS_{106}$-b-$POEGA_{17}$ NPs (10 mg/mL) were incubated for 0.5, 1, 2, and 4 h in either PBS or 10% FBS and particle size distributions were measured by DLS. After incubation with either PBS or 10% FBS, NPs were passed through a 0.45 mm syringe filter and used for hydrodynamic diameter (DO measurements, employing a Malvern Zetasizer Nano-ZS (Malvern Instruments Ltd, Worcestershire, UK) equipped with a 4 mW He—Ne laser operating at λ=632.8 nm.

Determination of Critical Micelle Concentration (CMC) and Hydrogen Peroxide- ($H_2O_2$—) Dependent Drug Release The CMC and $H_2O_2$-dependent drug release of $PPS_{106}$-b-$POEGA_{17}$ NPs were quantified as previously described (Gupta et al., J. Control Rel. 162:591-598, 2012). In both cases, Nile Red (NR) was used as a surrogate drug due to its fluorescence properties (fluoresces strongly only while in hydrophobic environment but is minimally fluorescent when released into aqueous phase where it is poorly soluble). Different dilutions were prepared from a 1 mg/mL stock solution to obtain NP samples ranging in concentration from 0.0001 to 1 mg/mL. Then, 10 mL of a 1 mg/mL NR stock solution in chloroform was added to 1 mL of each NP sample and incubated overnight in the dark at room temperature. The next day, samples were filtered with a 0.45 mm syringe filter and their Nile red fluorescence was measured in 96 well plates using a micro-plate reader (Tecan Infinite 500, Tecan Group Ltd., Mannedorf, Switzerland) at an excitation wavelength of 535±20 nm and an emission wavelength of 612±25 nm. The CMC was defined, as previously described, as the intersection on the plot of the Nile red fluorescence versus the copolymer concentration (Coutinho et al., J. Phys. Chem. B 106:12841-12846, 2002). The CMC was also confirmed by the observation of size and morphological changes on DLS.

To prepare 1% NR loaded NP solution, 50 mL of a 1 mg/mL NR stock solution in chloroform was added to 5 mL of NP solution (1 mg/mL). The residual chloroform was removed by incubation overnight in the dark at room temperature. The next day, samples were filtered using a 0.45 mm syringe filter prior to use. NR-loaded NPs were exposed to a range of concentrations (0-1000 mM) of hydrogen peroxide. Fluorescence intensity of NR was monitored in a 96 well plate using a micro plate reader (Tecan Infinite 500) at an excitation wavelength of 535±20 nm and an emission wavelength of 612±25 nm. Release of the dye due to NP oxidation and destabilization was assessed over time based on disappearance of NR fluorescence. The loss of fluorescence for each sample at each time point was determined by subtracting the fluorescent value from that of the sample prior to H₂O₂ addition, and the percent fluorescence remaining was determined by normalization to the same value (before addition of $H_2O_2$). This value for percent fluorescence remaining was subtracted from 100% and expressed as a percent release for each sample at each time point.

Fluorescent Imaging of 1483 HNSCC Cancer Cells In Vitro

Human 1483 head and neck squamous cell carcinoma (HNSCC) cells were plated on MatTek dishes and allowed to adhere. After adhering, the cells were treated with either empty $PPS_{106}$-b-$POEGA_{17}$ micelles (5), FA loaded $PPS_{106}$-b-$POEGA_{17}$ micelles (6), or 5-ROX-loaded $PPS_{106}$-b-$POEGA_{17}$ micelles (7) as prepared above in PBS (−/−) for 50 min at 1.3 µM. Cells were then rinsed 3 times with Hanks balanced salt solution (HBSS)/Tyrode's buffer, and the medium was replaced by DMEM/F12 with 5% FBS. After 50 min, the cells were rinsed 1 time with HBSS/Tyrode's buffer and imaged at 40× magnification, 0.65 objective using a fluorescence microscope (Leica DM IL LED FIM).

FA-NP treated cells were the only group that showed fluorescence in vitro. Lysotracker experiments (not shown) suggest that the intact FA-NPs are internalized though endocytosis, and that the lipiphilicity of FA (Log P=~6.0) allows for diffusion through endo/lysosomal membranes to reach COX-2 within the cytosol without requiring endosomal disruption. The lack of measurable fluorescence in cells treated with 5-ROX-NPs confirms that specific binding to COX-2 is required for effective visualization of COX-2-overexpressing cells following a "wash-out" incubation stage.

In Vivo Imaging of COX-2 in Inflammation

Carrageenan (50 µL 1% in sterile saline) was injected in the rear right footpad of Sprague Dawley rats (350-400 g), followed by micelle 6 (1 mg/kg FA, i.p.) at 2 h post-carrageenan. Animals were imaged 3 h later in a Xenogen IVIS 200 (DsRed filter, 1.5 cm depth, 1 s). For blocking COX-2, animals were pre-dosed with indomethacin (2 mg/kg, i.p.) 1 h prior to micelle 6 injection.

COX-2-derived prostaglandins are major contributors to the acute inflammation that develops 2 h after carrageenan injection into the paw in this model. The inflamed footpad model is ideal for imaging inflammation because it enables a direct comparison with the vehicle-injected contralateral footpad. After i.p. injection, FANPs (1 mg/kg FA) targeted the inflamed rat footpad with an average 10-fold increase in fluorescence over that of the contralateral control footpad (p<0.002), and the uptake was efficiently blocked by pre-treatment with the nonselective COX inhibitor indomethacin (FIG. 2A through 2C). The results in the rat footpad inflammation model demonstrate that FA-NPs effectively target sites of inflammation in vivo in order to visualize COX-2 in carrageenan induced edema. The blocking study further confirms that the FA molecule is released from the nanoparticle and is able to engage COX-2.

Establishment of Xenografts in Nude Mice

Female nude mice were purchased at 6-7 weeks of age from Charles River Labs. Human 1483 HNSCC cells were trypsinized and re-suspended in cold PBS containing 30% Matrigel such that 1×10⁶ cells in 100 µL were injected subcutaneously on the left flank. Tumors were allowed to grow for 2-3 weeks.

In Vivo Imaging of Nude Mice with Xenografts.

Female nude mice bearing 1483 xenograft tumors (800-1000 mm³) on the left flank were dosed with FA-NPs or 5-ROX-NPs (1 mg/kg FA or 5-ROX) by i.p. or tail vein injection. The animals were lightly anesthetized with 2% isoflurane for fluorescence imaging in the Xenogen IVIS 200 with the cy5.5 filter at 1.5 cm depth and 1 s exposure (f2). For the COX-2 active site blocking experiments, nude mice bearing 1483 xenografts were pre-dosed by injection with indomethacin (2 mg/kg, i.p.) 1 h prior to dosing with FA-NPs (1 mg/kg FA, i.p.).

FA-NPs were evaluated for COX-2 detection in 1483 HNSCC tumor xenografts in vivo. COX-2 imaging was performed after i.p. administration to mimic previous administration methods for FA in DMSO. In mice injected i.p. with FA-NPs (1 mg/kg FA), no fluorescence was observed in the tumor during the first 30 min post-injection, but signal was reproducibly detected in the COX-2-expressing 1483 tumors at 3-4 h post-injection. Whether fluorescence observed in the tumors was due strictly to nanoparticle accumulation within the tissue was evaluated by EPR effect or also by release of the FA molecule and its binding to COX-2. To this end, nude mice with 1483 xenografts were pretreated with either DMSO or indomethacin in DMSO (2 mg/kg, i.p.) prior to FA-NPs dosing (1 mg/kg FA, i.p.). At 4 h post-injection, the vehicle-pretreated mice showed strong fluorescence in their tumors, whereas the tumors of the indomethacin-pretreated mice displayed significantly lower fluorescence (p=0.003, FIGS. 3D and 3E). Lastly, 5-ROX-NPs which have no specific COX-2 binding moiety were administered and yielded similar fluorescent signal within tumors in indomethacin pre-treated mice and significantly lower fluorescent signal than tumors in FA-NP-treated mice (p=0.005). These observations collectively confirm that FA is released from FA-NPs to bind specifically with COX-2, increasing retention within tumors.

Pharmacokinetics and Biodistribution

Wild-type CD-1 mice (4-6 weeks old, Charles River) were injected via the tail vein with FA-NPs (1 mg/kg FA). Mice were euthanized at 15, 30, 60, 120, and 240 min, blood was collected by cardiac puncture into a heparinized syringe and transferred into a 1.5 mL heparinized tube on ice followed by dissection and collection of major organs such as liver, lung, heart, kidney, and spleen. The blood samples were centrifuged at 4° C. at 6000 rpm for 5 min, and the plasma was transferred to clean tubes and frozen at −80° C. FA was extracted by homogenizing plasma samples in 100 mM Tris, pH 7.0, buffer and mixing an aliquot of the homogenate with 1.2× volume of acetonitrile. The acetonitrile was removed and the samples were dried, reconstituted and analyzed via reversed phase HPLC-UV using a Phenomenex 10×0.2 cm C18 or a Phenomenex 7.5×0.2 cm Synergi Hydro-RP column held at 40° C. The samples were quantified against a standard curve prepared by adding FA to homogenates of un-dosed animals followed by the workup described. Collected organs were imaged on an IVIS Lumina III system (excitation filter: 580±5 nm, emission filter: 620±5 nm) and the images were analyzed for photon counts for statistical analysis.

FA-NPs had a 1.1 h plasma half-life after the single administration. FA fluorescence was measured in organs of interest ex vivo at each time point after FANP administration. The FA-NPs biodistributed most to the liver, kidney, and lungs early after administration. Interestingly, no high fluorescence was observed within the spleen, a major MPS organ typically associated with nanoparticle clearance. The kinetics of organ biodistribution correlated well with FA-NP persistence in the blood, with amount of FA-NPs in all organs decreasing at similar rates to FA-NP blood clearance. Importantly, the fluorescent signal in non-targeted major organs nearly returns to baseline by 4 h post-injection, indicating that this is an ideal time point for imaging target sites with little background noise.

Figure 5:
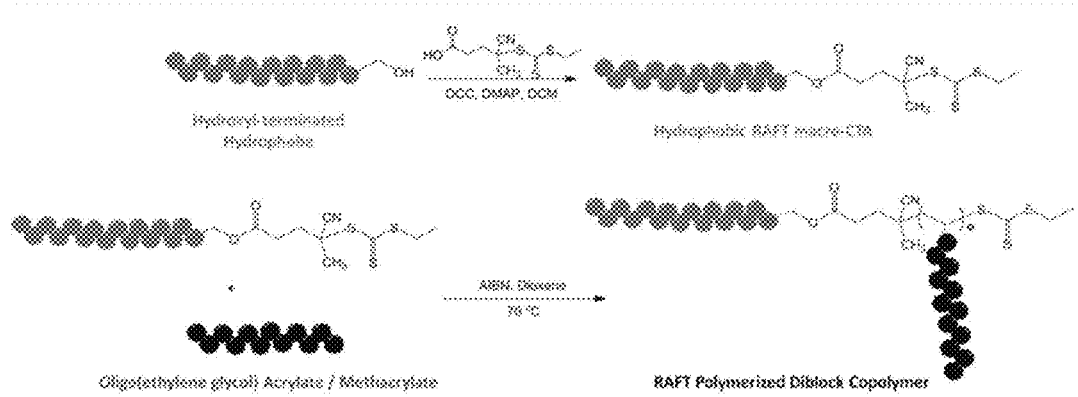
FIG. 5 is a schematic of a diblock copolymer as disclosed herein where a hydrophobic block is coupled to a poly[oligo(ethylene glycol)$_9$ (meth)acrylate.
Figure 6:
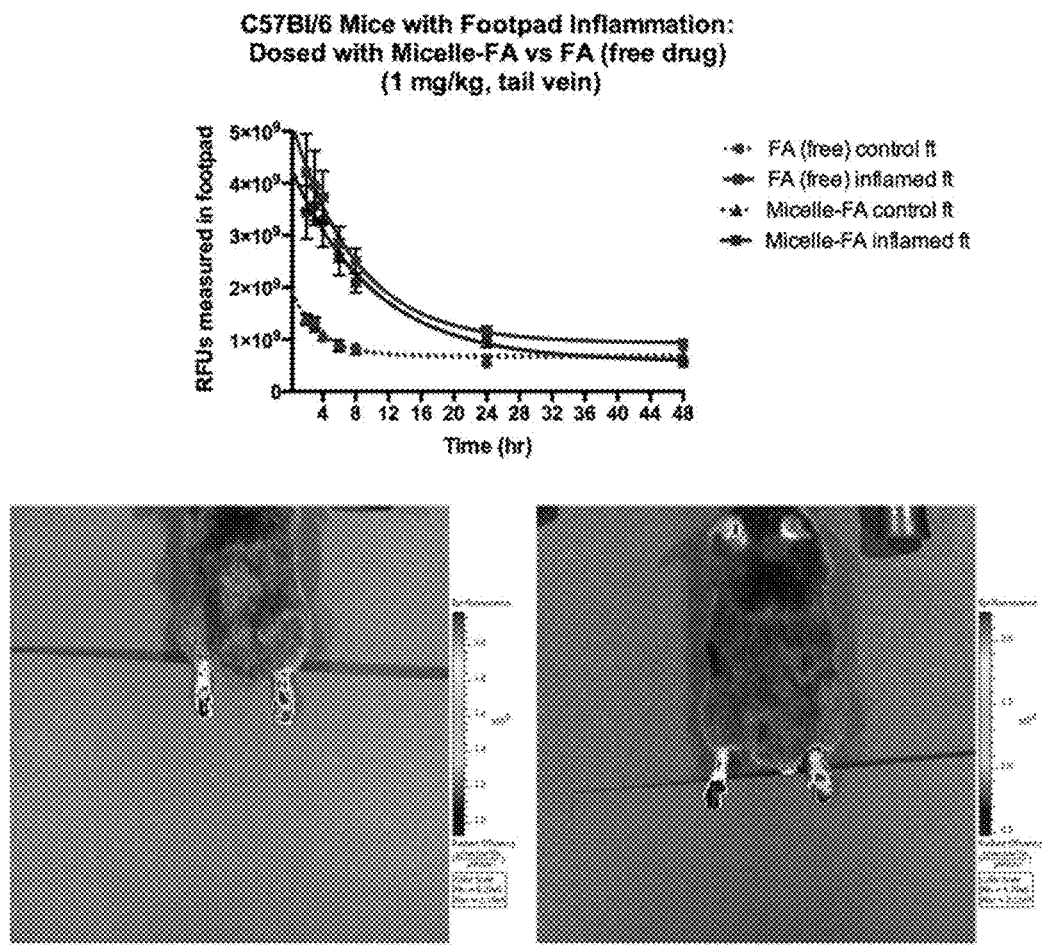
FIG. 6 is a comparison of mice with footpad inflammation dosed with micelle 6 or free FA.
Figure 7:
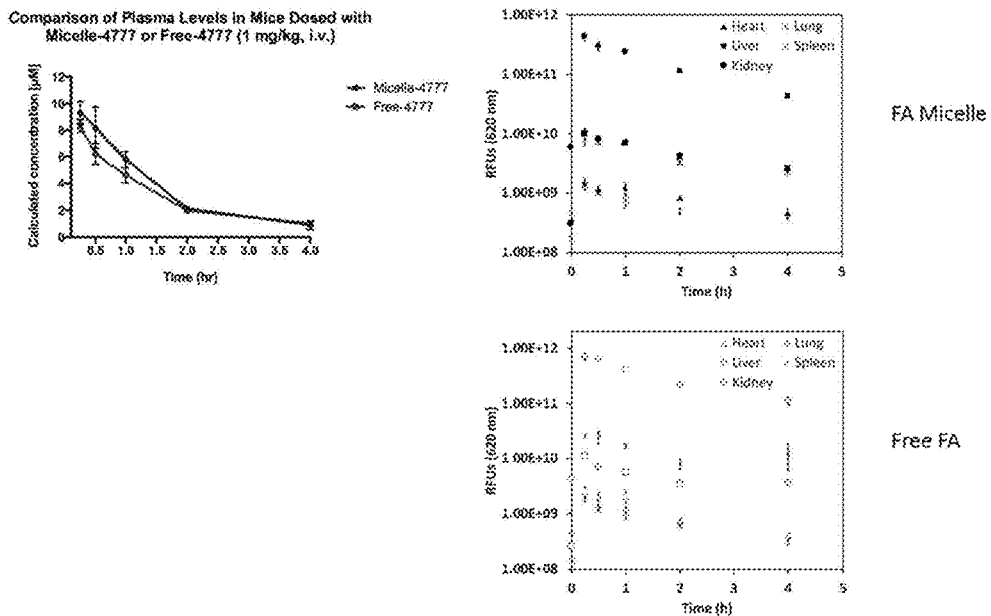
FIG. 7 is a comparison of plasma levels in mice dosed with micelle 6 or free micelle 5.

The pharmacokinetics, biodistribution, uptake, and retention of FA-NPs in animal models of cancer and inflammation were monitored after a single i.v. administration. Nude mice bearing 1483 HNSCC xenografts were administered FA-NPs (1 mg/kg FA, i.v.) and tissues of interest (tumor, liver, kidney, lung, and muscle control) were excised and imaged ex vivo after 4 h. Remarkably, maximal signal was documented in the tumor even without normalization to tissue weight, with raw tumor fluorescence intensity detected over 2-fold above raw liver fluorescence intensity (FIGS. 3G and 3H). To investigate the kinetics of FA-NP uptake and retention at sites of inflammation following i.v. delivery, the inflamed footpads of C57BL/6 mice were imaged beginning 24 h after carrageenan-induced edema (100 mL, 1%). A mouse model was chosen for this experiment due to the slow resolution of inflammation and extended time course of COX-2 expression within this model (up to 48 h compared to only 5 h in the rat model). Inflamed footpads of mice dosed with FA-NPs (1 mg/kg FA, i.v.) had up to 3-fold higher fluorescence relative to the contralateral control footpads throughout the time course (FIG. 5). Maximal signal was detected at the first time point measured (2 h postinjection), and signal was detected above background over 8 h post-injection of FA-NPs. The high retention of FA-NPs within inflamed footpads between 4 and 8 h is in contrast to the retention in other major organs after 4 h; this result further supports that 4-8 h is the optimal window for imaging in order to achieve high signal-to-noise (SNR) in the inflamed and/or cancerous tissue. Amplex Red was used to quantify $H_2O_2$ within both the inflamed and contralateral tissues, showing over 2-fold increase in ROS-production within the inflamed tissue. The concomitant overexpression of COX-2 and ROS-production within inflamed tissue likely increases both release of FA from FA-NPs and molecular engagement of FA with COX-2 at these sites, contributing to the high SNR achieved over contralateral tissue.

In Vivo Toxicology

Wild-type CD-1 mice (4-6 weeks old, Charles River) were injected via the tail vein with either saline or FA-NPs (1, 10, and 20 mg/kg FA). Blood and major organs (heart, lungs, liver, spleen, and kidneys) were collected 24 h after FA-NP injection. Serum was obtained by incubating whole blood at room temperature for 30 min and centrifuging at 3,000 g for 5 min. Serum alanine aminotransferase (ALT), aspartate aminotransferase (AST), and blood urea nitrogen (BUN) were measured by the Vanderbilt TPSR using a commercially available Transaminase-CII kit and Blood Urea Nitrogen Test (Wako), respectively. Major organs were fixed immediately in 10% neutral buffered formalin, embedded, sliced 5 mm thick, and stained with hematoxylin and eosin (H&E). Slides were blindly reviewed by a board certified pathologist for organ toxicity.

Figure 8A:
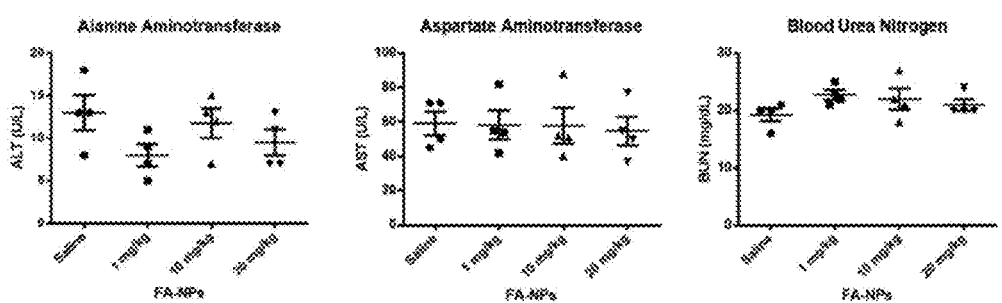
FIGS. 8A and 8B show in vivo toxicology of FA-NPs after i.v. administration.
Figure 8B:
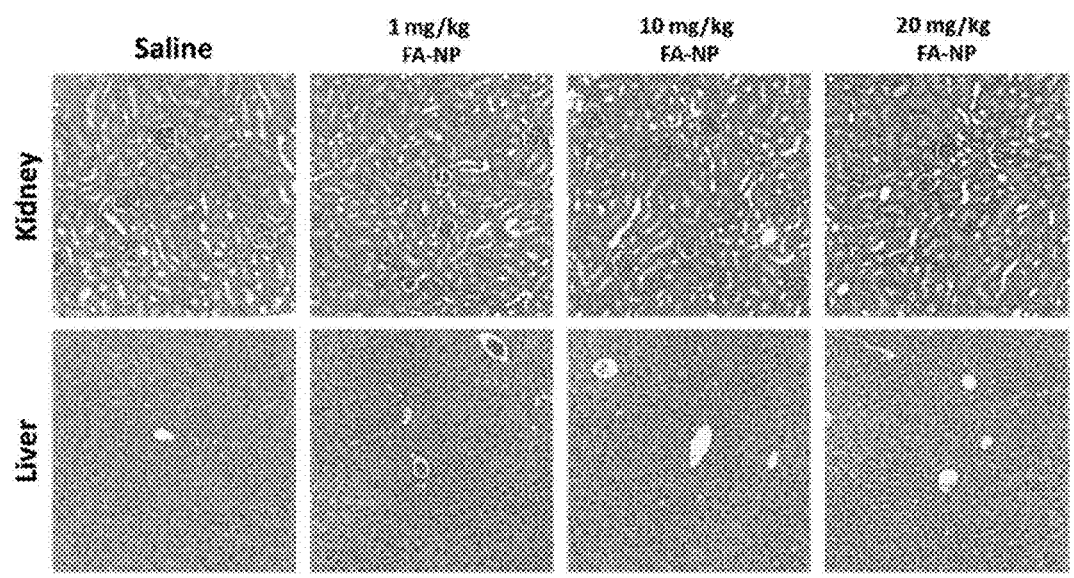

To test the safety profile of FA-NPs, we i.v. administered the lowest effective imaging dose (1 mg/kg FA) as well as 10× (10 mg/kg FA) and 20× (20 mg/kg FA) higher doses. Biochemical analysis of liver (ALT and AST) and kidney (BUN) toxicity and histological analysis of major organ (heart, lungs, liver, spleen, and kidneys) toxicity was performed 24 h post-injection. No significant increase in serum markers of liver and kidney toxicity were observed compared to saline treated mice at any dose administered (FIG. 8A). Moreover, major organs were observed by a blinded, board certified pathologist, and no apparent toxicity was seen within any treatment groups (FIG. 8B).

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A composition, comprising: a cyclooxygenase-2-selective therapeutic and/or diagnostic agent having a therapeutic and/or diagnostic agent conjugated to a NSAID drug; and a ROS-responsive nanoparticle, wherein the ROS-responsive nanoparticle comprises a plurality of diblock copolymers, and wherein the diblock copolymers comprise a poly(propylene sulfide) block having from 2 to 200 propylene sulfide residues and a poly(oligo(ethylene glycol) methyl ether acrylate) block having from 2 to 50 oligo(ethylene glycol) methyl ether acrylate residues.

2. The composition of claim 1, wherein the NSAID drug is selected from the group consisting of fenamic acids, indoles, phenylalkanoic acids, phenylacetic acids, coxibs, pharmaceutically acceptable salts thereof, and combinations thereof.

3. The composition of claim 1, wherein the NSAID drug is selected from the group consisting of aspirin, o-(acetoxyphenyl)hept-2-ynyl sulfide (APHS), indomethacin, 6-methoxy-α-methyl-2-naphthylacetic acid, meclofenamic acid, 5,8,11,14-eicosatetraynoic acid (ETYA), diclofenac, flufenamic acid, niflumic acid, mefenamic acid, sulindac, tolmetin, suprofen, ketorolac, flurbiprofen, ibuprofen, aceloferac, alcofenac, amfenac, benoxaprofen, bromfenac, carprofen, clidanac, diflunisal, efenamic acid, etodolic acid, fenbufen, fenclofenac, fenclorac, fenoprofen, fleclozic acid, indoprofen, isofezolac, ketoprofen, loxoprofen, meclofenamate, naproxen, orpanoxin, pirprofen, pranoprofen, tolfenamic acid, zaltoprofen, zomepirac, celecoxib, pharmaceutically acceptable salts thereof, and combinations thereof.

4. The composition of claim 1, wherein the NSAID drug is selected from the group consisting of indomethacin, celecoxib, pharmaceutically acceptable salts thereof, and combinations thereof.

5. The composition of claim 1, wherein the cyclooxygenase-2-selective therapeutic and/or diagnostic agent has the diagnostic agent and the diagnostic agent comprises a fluorescent molecule selected from the group consisting of a fluorophore, a cyanine dye, and a near infrared (NIR) dye.

6. The composition of claim 5, wherein the diagnostic agent is 6-carboxy-X-rhodamine, Cy5, Cy5.5, and Cy7, NIR641, NIR664, NIR700, and NIR782.

7. The composition of claim 5, wherein the diagnostic agent is 5-carboxy-X-rhodamine.

8. The composition of claim 1, wherein the cyclooxygenase-2-selective therapeutic and/or diagnostic agent is:

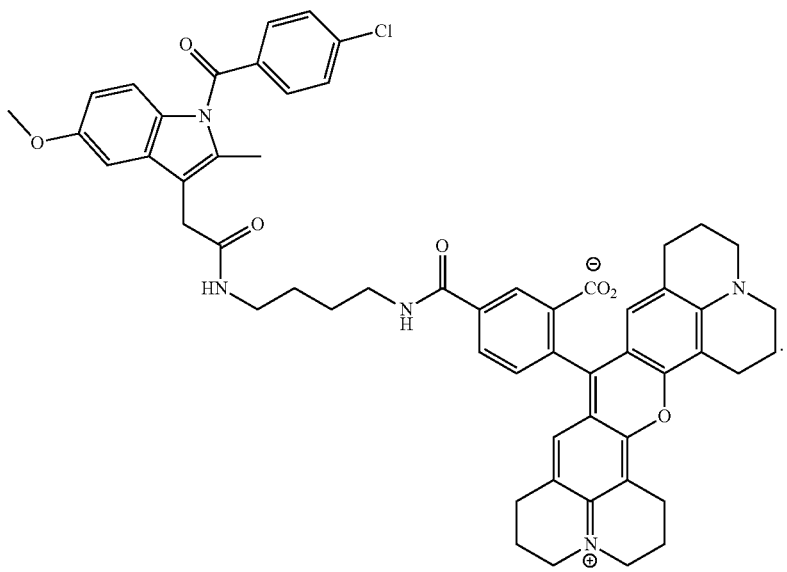

Fluorocoxib A (FA)

9. The composition of claim 1, where the poly(propylene sulfide) block has from 80 to 100 propylene sulfide residues.

10. The composition of claim 1, wherein the ROS-responsive nanoparticle comprises a plurality of poly(propylene sulfide)$_{106}$-b-poly[oligo(ethylene glycol)$_9$ methyl ether acrylate]$_{17}$ copolymers.

11. A method of diagnosing a disease characterized by COX-2 expression or over expression in a subject, comprising administering to the subject the composition of claim 1, and detecting a signal from the composition.

12. The method of claim 11, wherein the disease is skin cancer, colon cancer, esophagus cancer, bladder cancer, or oropharynx cancer.

13. The method of claim 11, wherein the composition is administered to the subject by intravenous injection.

* * * * *

UNITED STATES PATENT AND TRADEMARK OFFICE
CERTIFICATE OF CORRECTION

PATENT NO. : 10,105,455 B2
APPLICATION NO. : 15/206798
DATED : October 23, 2018
INVENTOR(S) : Craig L. Duvall et al.

It is certified that error appears in the above-identified patent and that said Letters Patent is hereby corrected as shown below:

In the Specification

Column 1, Line 13, cancel the text "This invention was made with government support under grant nos. CA89450 and CA136465 awarded by the National Institutes of Health. The government has certain rights in the invention"
And replace it with the following text:
--This invention was made with government support under grant numbers CA089450 and CA136465 awarded by the National Institutes of Health. The government has certain rights in the invention.--

Signed and Sealed this
Eighth Day of October, 2019

Andrei Iancu
*Director of the United States Patent and Trademark Office*